United States Patent [19]

Revici et al.

[11] Patent Number: 4,513,008

[45] Date of Patent: Apr. 23, 1985

[54] VIRUCIDAL COMPOSITIONS AND THERAPY

[75] Inventors: Emanuel Revici, New York, N.Y.; Bob E. Sherwood; Herman P. Benecke, both of Columbus, Ohio; John M. Rice, Westerville, Ohio; Richard W. Geisler, Houston, Tex.

[73] Assignee: The Vinoxen Company, Inc., Houston, Tex.

[21] Appl. No.: 404,199

[22] Filed: Jul. 30, 1982

[51] Int. Cl.³ ............... A61K 31/20; A61K 31/11; A61K 31/045

[52] U.S. Cl. .................... 514/560; 514/703; 514/739; 424/45

[58] Field of Search ........... 424/318, 333, 343, 45

[56] References Cited

U.S. PATENT DOCUMENTS 4,097,602  6/1978  Silver ..................... 424/317

OTHER PUBLICATIONS

Lapedes, Daniel N., Editor in Chief, McGraw-Hill, Dictionary of Scientific and Technical Terms, pp. 30 and 585.

*Primary Examiner*—Albert T. Meyers
*Assistant Examiner*—John W. Rollins
*Attorney, Agent, or Firm*—Millen & White

[57] ABSTRACT

A method of inactivating enveloped virus comprises contacting said virus with a virucidally effective amount of a $C_{20-24}$ linear polyunsaturated acid, aldehyde or primary alcohol having 5-7 double bonds, a pharmaceutically acceptable salt of said acid, or a mixture thereof. Topical administration of the virucide is preferred and is effective in treating lesions associated with herpes infections. Pharmaceutical compositions for use in the present method are provided.

16 Claims, No Drawings

VIRUCIDAL COMPOSITIONS AND THERAPY

BACKGROUND OF THE INVENTION

This invention relates to virucides and in particular to a method of inactivating enveloped virus. In a composition of matter aspect, the invention relates to a pharmaceutical composition for use in the present method.

Viral infections have in the past been largely resistant to antibiotic therapy. In particular, herpes infections have proven to be especially refractory. Herpes virus belongs to the class known as 'enveloped virus", by which is meant those DNA or RNA virus having a lipoprotein envelope. Normally, the virus envelope is derived from host membrane components under the direction of viral protein. The class of enveloped virus includes herpes virus, e.g., herpes simplex 1 and 2; myxovirus, e.g., influenza virus; paramyxovirus, e.g., virus responsible for measles and mumps, and respiratory syncitial virus responsible for croup; corona virus, which is also implicated in the common cold; and toga virus, e.g., rubella virus and virus responsible for encephalitis and hemorrhagic fever.

Many compounds have antiviral or virustatic activity, i.e., they inhibit the spread of viral infection by inhibiting the replication of virus particles. However, they do not inactivate the virus. Acyclovir, 9-(2-hydroxyethoxymethyl)guanine, an antiviral drug which has recently been cleared by the FDA for use in treating herpes infections in humans, is a virustatic agent, but not a virucide.

Recent research has shown that certain lipophilic compounds inhibit replication of some enveloped virus in vitro. Sands, Antimicrobial Agents and Chemotherapy, 12, 523–528 (1977), discloses that various fatty acids can inhibit viral replication in bacteriophage, and that at least two modes of fatty acid inhibition can be involved. The first mode involves inactivation of the virus, i.e., virucidal activity. Oleic acid, a monounsaturated $C_{18}$ fatty acid, was the most effective fatty acid tested for this property, but a $C_{18}$ acid having two double bonds was essentially inactive. The second method is inhibition of replication, without killing the virus, i.e., anti-viral or virustatic activity. This phenomenon is related to the stage in the infectious cycle in which the fatty acid is added.

Reinhardt et al., J. Virology, 25, 479–485 (1978) disclose that unsaturated fatty acids can inhibit the viral replication of PR4 bacteriophage in vitro. The most effective acids were oleic acid and palmitoleic acid. Arachidonic acid ($C_{20}$ tetraene) was moderately effective, but less effective than linolenic acid ($C_{18}$ triene).

Kabara et al., Antimicrobial Agents and Chemotherapy, 2, 23–28 (1972) disclose that certain fatty acids inhibit the growth of gram-positive and gram-negative microorganisms, but no virus species were tested. Some saturated fatty acids had antibacterial activity, mono-unsaturated acids were more effective and dienoic acids were even more active, for $C_{18}$ fatty acids. However, arachidonic acid was not inhibitory at the concentrations tested.

Sands et al., Antimicrobial Agents and Chemotherapy, 15, 67–73 (1979) disclose antiviral activity in vitro of $C_{14-20}$ unsaturated alcohols having 1-4 double bonds, the most active being gamma-linolenyl alcohol (6,9,12-octadecatrien-1-ol), while a $C_{20}$ tetraenyl alcohol had low activity. Lower antiviral activity in vitro was disclosed for saturated alcohols by Snipes et al., Ibid., 11, 98–104 (1977); and Snipes et al., Symp. Pharm. Effects Lipids (AOCS Monograph No. 5), 63–74 (1978).

A need continues to exist for a virucidal agent which is active against enveloped virus and which has very low toxicity, especially one that is a potent topical virucide against herpes virus.

OBJECTS OF THE INVENTION

One object of the present invention is to provide a method for inactivating enveloped virus using an agent of low human cytotoxicity.

Another object of the present invention is to provide a topical virucidal agent which is effective to prevent and/or reduce lesions which accompany herpes infections in animals and humans.

A further object of the present invention is to provide a pharmaceutical composition for use in the foregoing methods.

Upon further study of the specification and appended claims, further objects and advantages of this invention will become apparent to those skilled in the art.

SUMMARY OF THE INVENTION

In a method aspect, the present invention provides a method of inactivating enveloped virus, which comprises contacting the situs of said virus or the virus itself with a virucidally effective amount of a $C_{20-24}$ linear polyunsaturated acid, aldehyde or primary alcohol having 5-7 double bonds, a pharmaceutically acceptable salt of said acid, or a mixture thereof.

In a preferred method of use aspect, the present invention provides a method of treating lesions associated with a herpes infection in an animal or human subject, which comprises applying to the inflamed area an amount of the foregoing virucidal agent effective for reducing or arresting said lesions.

In a composition of matter aspect, the present invention provides a pharmaceutical composition comprising a virucidally effective amount of the foregoing virucidal agent, and a pharmaceutically acceptable carrier. Preferred such compositions suitable for topical application are also provided.

DETAILED DISCUSSION

The $C_{20-24}$ linear polyunsaturated acids suitable for use in the present method and composition include eicosapentaenoic acid (EPA), eicosahexaenoic acid, eicosaheptaenoic acid, heneicosapentaneoic acid, heneicosahexaenoic acid, heneicosaheptaenoic acid, docosapentaenoic acid, docosahexaenoic acid (DHA), docosaheptaenoic acid, tricosapentaenoic acid, tricosahexaenoic acid, tricosaheptaenoic acid, tetracosapentaenoic acid, tetracosahexaenoic acid, tetracosaheptaenoic acid and mixtures thereof. Preferred acids are EPA, DHA and mixtures thereof, including both non-conjugated and conjugated double bond isomers. Especially preferred are 5,8,11,14,17-EPA and 4,7,10,13,16,19-DHA and mixtures thereof. It will be appreciated that the foregoing polyunsaturated acids can exist in a variety of geometric isomers, all of which are included in the invention.

The polyunsaturated acids may be employed as pure compounds or mixtures of pure compounds, or they may be employed as concentrates derived from natural vegetable and/or animal sources. Important natural sources of the polyunsaturated acids suitable for use in the invention are fish liver oils and concentrates and/or extracts thereof. It is known that EPA and DHA are present in significant quantities in oils such as cod liver oil, halibut liver oil, tuna liver oil and the like. Saponification and/or solvent extraction of fish liver oils can increase the percentage of free polyunsaturated fatty acids available therefrom by subsequent concentration and/or further extraction.

The $C_{20-24}$ linear polyunsaturated acids which are not available from natural sources may be synthesized by conventional techniques for producing long-chain polyolefins having either cis or trans double bonds. Such olefin syntheses are disclosed generally in the chapters on olefin synthesis in Harrison et al., "Compendium of Organic Synthetic Methods" (Wiley 1971); and Carruthers, "Some Modern Methods of Organic Synthesis" (Cambridge 1971); and with respect to the closely related carotene systems, in Anand et al., "Art in Organic Synthesis" (Holden-Day 1970), the foregoing being illustrative and not inclusive of all such general references. The carboxyl group can be introduced early, as a protected, e.g., esterified, function, or at the end of the synthetic pathway, by conventional means, as illustrated in the foregoing references. The longer chain acids may also be obtained by homologation of acids having fewer atoms in the carbon chain, by conventional reaction sequences, e.g., Arndt-Eistert homologation, and the like.

The various geometric and position isomers of the polyunsaturated acids and/or the alcohols and aldehydes related thereto may be obtained by one or more conventional separation techniques well known in the art, e.g., column chromatography, thin layer chromatography, vapor phase chromatography, high performance liquid chromatography, fractional crystallization, and the like. Partial separations, e.g., solvent extraction, molecular distillation, for the purpose of producing more highly active virucidal fractions are also included within the separation methods envisioned for the production of virucidal agents for use in the present method and composition.

The polyunsaturated acids of the invention may be administered in the form of pharmaceutically acceptable addition salts with inorganic or organic bases, where the salts possess comparable and/or otherwise advantageous virucidal activity and which are otherwise physiologically compatible. Suitable inorganic bases to form these salts include, e.g., the hydroxides, carbonates, bicarbonates or alkoxides of the alkali metals or alkaline earth metals, e.g., sodium, potassium, magnesium, calcium and the like. Suitable organic bases include the following amines; lower mono-, di-, and trialkylamines, the alkyl radicals of which contain up to three carbon atoms, e.g., methylamine, dimethylamine, trimethylamine, ethylamine, di- and triethylamine, N-methyl-N-ethylamine, and the like; mono-, di- and trialkanolamines, the alkano radicals of which contain up to three carbon atoms, e.g., mono-, di- and triethanolamine, alkylene-diamines which contain up to six carbon atoms, e.g., hexamethylenediamine; phenylalkylamines, e.g., benzylamine, phenylethylamine and N-methylphenylethylamine; cyclic saturated or unsaturated bases containing up to six carbon atoms, e.g., pyrrolidine, piperidine, morpholine, piperazine and their N-alkyl and N-hydroxyalkyl derivatives, e.g., N-methylmorpholine and N-(2-hydroxyethyl)piperidine, as well as pyridine.

Furthermore, there may be mentioned the corresponding quaternary salts, e.g., the tetraalkyl, e.g., tetramethyl, alkylalkanol, e.g., methyltrimethanol and trimethylmonoethanol, and cyclic ammonium salts, e.g., the N-methylpyridinium, N-methyl-N-(2-hydroxyethyl)-morpholinium, N,N-dimethylmorpholinium, N-methyl-N-(2-hydroxyethyl)morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid in water containing at least one equivalent amount of a hydroxide, carbonate, or bicarbonate corresponding to the inorganic salt desired. Advantageously, the reaction is performed in a water-miscible, inert organic solent for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, e.g., a lower alkanol, e.g., butanol, or a lower alkanone, e.g., ethyl methyl ketone, gives the solid inorganic salt if that form is desired.

To produce an amine salt, the acid is dissolved in a suitable solvent of either moderate or lower polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of low polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid with an equivalent amount of the corresponding quaternary ammonium hydroxide in water solution, followed by evaporation of the water.

The $C_{20-24}$ aldehydes and primary alcohols suitable for use in the method and composition of the invention correspond to the acids set forth above, except that the carboxyl group of the acids is replaced by a formyl group or a hydroxymethylene group, respectively. The aldehydes and alcohols similarly exist as various geometric isomers which are included in the scope of this invention.

The primary alcohols and aldehydes may be readily prepared, e.g., by reduction of the corresponding acids, or by other conventional methods. Typically, an acid will be converted to, e.g., a methyl ester, and the ester will be reduced to the corresponding alcohol with a hydride reducing agent, e.g., $LiAlH_4$. The ester, optionally a triglyceride, is converted to the corresponding aldehyde by the method of Gauglitz, Jr. et al., J. Am. Oil Chem. Soc., 37, 425 (1960).

Other conventional techniques for producing an aldehyde or alcohol having the same carbon chain length or having fewer or greater numbers of carbons in the chain are also well known to the art, and are also illustrated inter alia in the aforementioned Harrison et al. reference. The alcohols may be converted to halides, sulfonate esters and the like and used as intermediates for the production of higher homolog alcohols, aldehydes and acids, e.g., by reaction with cyanide, followed by hydrolysis or hydride reduction, or by other conventional synthetic pathways. It may be convenient and/or advantageous to use mixtures of reactants and products from the foregoing synthetic pathways, without further separation, as virucidal agents.

The foregoing examples of virucidal compounds useful in the present invention are intended to be illustrative of the scope of the invention, but not limitative thereof, and the invention includes equivalents of the illustrated compounds that also achieve the disclosed virucidal effects. Contemplated equivalents include mono or polysubstitution of moieties on the polyunsaturated alcohols, aldehydes, acids and salts that will not interfere with their virucidal activity. Suitable such substituents would include halogen atoms, lower alkyl, lower alkoxy, hydroxy and the like, which can be introduced by conventional means.

Isomerization of the double bonds in the polyunsaturated alcohols, aldehydes and acids of the invention may be effected by treatment with various basic catalysts. The aldehyde function should be protected in the form of a base-stable derivative, e.g., an acetal, or should be introduced after isomerization. Typically, a polyunsaturated acid, e.g., a pure acid or a mixture of acids from e.g., a natural marine oil, which usually has an arrangement of double bonds in allylic relation to one another, is treated with a concentrated solution of alkali and heated to promote double bond isomerization. Concentrated aqueous alkali, e.g., 50% KOH, or alkali metal alkoxides in polar solvents, are effective for isomerizing such allylic double bonds. The resultant acids contain double bonds which are partially or fully conjugated, i.e., they form alternating single and double bonds. Accordingly, the progress of the isomerization reaction may be monitored with ultraviolet spectroscopy, which reveals the presence of conjugated double bond systems by the appearance of absorption peaks in the long wavelength end of the ultraviolet spectrum. Isomerization preferably is effected under an inert gas atmosphere to avoid oxidation of the polyene systems.

The polyunsaturated alcohols, aldehydes, acids and salts of the invention, in contrast to the majority of drugs on the market for use in treating viral infections, are unusual in that they have virucidal activity, i.e., they disrupt the virus particles themselves and render them inactive and permanently non-infectious. Is is especially noteworthy that the present compounds are potent topical virucides against enveloped virus, both in vitro and in vivo. They are especially effective for the treatment of lesions produced as a result of herpes virus infections, e.g., oral, genital, ocular and the like. In fact, the topical activity of at least the preferred species against herpes simplex virus type 2 (HSV-2) is at least comparable to, and in some preparations superior to, that of Acyclovir (ACV).

The compounds of the invention appear to prolong the survival time of animals infected with herpes virus, as well as being effective in reducing the formation of lesions. This suggests that the compounds of the invention have systemic activity.

The virucidal properties of the compounds of the invention suggest their use to prevent the spread of infection by enveloped virus, e.g., by incorporating them in a hand cream or lotion for use by physicians both before and after the examination of patients with suspected virus infections. Furthermore, the compounds may be used in fluids used to kill virus on examining tables, instruments, gloves, towels and other surfaces which might come in contact with virus particles during the course of medical examinations. The low toxicity of the compounds of the invention further enhances their attractiveness for such prophylactic use.

Evidence of the efficacy of the virucides of the invention in vitro has been obtained from bioassay using HSV-2, using a standard assay procedure. Serial dilutions of the compounds were tested for their ability to prevent plaque formation by a stock virus suspension. Reduction of plaque titer by test compounds as compared to mock treated controls was indicative of virucidal activity. Minimal inhibitory concentrations (MIC) of the test compounds, defined as the lowest concentration of the test compound capable of producing a 3-log (1,000 fold) reduction in virus titer, were determined. These represent the upper limit for the drug concentration, since dilutions were not carried beyond 1:6400 and in some cases 1:12800. At a dilution of 1:12800, EPA had an MIC of 0.37 $\mu$g/ml and DHA had an MIC of 0.47 $\mu$g/ml. A purified fraction isolated from cod liver oil hydrolysate had an MIC of 0.42 $\mu$g/ml, while a less highly purified hydrolysate fraction had an MIC of 1.00 $\mu$g/ml. Cod liver oil itself was inactive.

As evidence of the excellent topical activity of the virucides of the invention against enveloped virus, in vivo tests were carried out in mice and in guinea pigs. These tests were effected using substantially the same procedures as those reported by Pancic et al., Antimicrobial Agents and Chemotherapy, 19, 470-476 (1981). In both studies, DHA was compared with ACV in a controlled study for effectiveness in reducing the occurrence and the severity of lesions resulting from infection by HSV-2 and in reducing mortality resulting from the virus infection. Surprisingly and unexpectedly, a low dose of DHA in an ointment base was highly effective in comparison with ACV in reducing lesions and in reducing mortality rates in mice. In fact, a low dose of DHA in the particular ointment vehicle used for test purposes appeared to have a higher activity than a high dose of the same material in the same vehicle.

While not wishing to be bound by any particular explanation of this phenomenon, it may be related to the action of fluid micelles formed by the fatty acid upon viral envelope proteins, which destabilize the viral membrane and inactivate the virus particle. It is known that lipid micelle formation and structure is sensitive to lipid concentration and to the composition of the suspending medium. Thus, it is possible that micelles with significantly different properties could be formed at higher concentrations or in different vehicles.

The compounds of this invention can be employed in mixture with conventional excipients, i.e., pharmaceutically acceptable organic or inorganic carrier substances suitable for parenteral or enteral application which do not deleteriously react with the active compounds. Suitable pharmaceutically acceptable carriers include but are not limited to water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, and the like. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or wheat starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, and the like.

A preferred mode of application of the virucides of the invention is as a topical agent, either in nonsprayable or sprayable form. Non-sprayable forms can be semi-solid or solid forms comprising a carrier indigenous to topical application and having a dynamic viscosity preferably greater than that of water. Suitable formulations include, but are not limited to, solutions, suspensions, emulsions, creams, ointments, powders, liniments, salves and the like. If desired, these may be sterilized or mixed with auxiliary agents, e.g., preservatives, stabilizers, wetting agents, buffers or salts for influencing osmotic pressure and the like. Preferred vehicles for non-sprayable topical preparations include ointment bases, e.g., polyethylene glycol-1000 (PEG-1000); conventional ophthalmic vehicles; creams, e.g., HEB cream; and gels, e.g., K-Y gel; as well as petroleum jelly and the like. These topical preparations may also contain emollients, perfumes and/or pigments to enhance their acceptability for various usages.

Also suitable for topical application are sprayable aerosol preparations wherein the virucidal compound, preferably in combination with a solid or liquid inert carrier material, is packaged in a squeeze bottle or in admixture with a pressurized volatile, normally gaseous propellant, e.g., a Freon(Chlorofluorocarbon) or environmentally acceptable volatile propellant. Such compositions can be used for application to environmental surfaces, e.g., examining tables, toilet seats and the like, and/or for application to the skin or to mucous membranes. The aerosol or spray preparations can contain solvents, buffers, surfactants, perfumes and/or antioxidants in addition to the virucidal compounds of the invention.

For the preferred topical applications, especially for treatment of humans and animals suffering from the symptoms of herpes virus infections, it is preferred to use the polyunsaturated acids of the invention, although the unsaturated alcohols and aldehydes are also suitable. Salts of the acids appear to be less effective for topical applications. It will be appreciated that salts can be used to prepare compositions for topical applications, in combination with suitable buffers and/or acids to lower the pH of the final preparation.

The virucides of the invention are generally administered to animals, especially mammals, in virucidally effective amounts, and in dosage unit form. The dose can be administered singly or as divided dosages throughout the day.

In the preferred topical form of administration used to effect the present method, application of a virucidally effective amount of a virucide according to the invention to an infected area, e.g., skin surfaces, mucous membranes, eyes, of an animal or human subject suffering from a viral infection, especially a herpes infection, will generally range from about 0.001 mg to about 1 g per application, depending upon the area to be treated, the severity of the symptoms and the nature of the virucidal agent and the topical vehicle employed. Preferably, dosages in the range 0.01–100 mg will be used. A preferred topical preparation is an ointment wherein about 0.01–50 mg of virucide is used per cc of ointment base, the latter being preferably PEG-1000, and more preferably an ointment containing about 0.1–10 mg/cc of a $C_{20-24}$ acid according to the invention, preferably DHA and/or EPA, in PEG-1000.

In preparing virucidal compositions according to the present invention, particularly topical preparations using polyunsaturated acids, it is preferable to use acids which are as pure as possible and/or which are substantially free, or have at least a significantly reduced content, of esters, e.g., triglycerides. Thus, where a fish liver oil is used as the source of the polyunsaturated acids, reduction of the natural triglyceride content, e.g., by saponification of the oil and recovery of the saponified acids fraction, will be advantageous.

Alternatively, molecular distillation, solvent extraction, fractional crystallization, liquid chromatography and the like are advantageously used to produce more concentrated and more active fractions. Combinations of the foregoing techniques can be used to achieve still more virucidally effective compositions.

Pharmaceutical preparations wherein substantially pure $C_{20-24}$ polyunsaturated acids having 5–7 double bonds are used are preferred, especially those which are substantially free of esters, e.g., triglycerides, and most preferably those having substantially pure EPA and/or DHA as substantially the only fatty acids therein. Where a concentrate of polyunsaturated acids is used to prepare the pharmaceutical composition, the content of $C_{20-24}$ fatty acids having 5–7 double bonds is advantageously at least about 20% by weight, 30% being preferred, and 40%, 50%, 60%, 70%, 80%, 90%, 95% and 99% being even more preferable the higher the percentage of the virucides. Conversely, the lower the triglyceride content, e.g., less than 50%, preferably less than 40%, 30%, 20%, 10%, 5% and most preferably less than 1%, the more preferred is the composition.

It will be understood that formulations and dosages may be varied and may fall outside of the preferred ranges for various uses, e.g., applications to environmental surfaces for prophylactic use and/or veterinary and disinfectant applications.

Aerosols for topical medicinal applications will have similar concentrations and dosages to the creams, lotions and ointments described above, but may have higher or lower concentrations for other applications, e.g., prophylactic and/or disinfectant use, veterinary applications and the like.

Dosage levels for enteral and/or parenteral administration to achieve systemic activity will generally fall in the range of 0.001 mg–5 g daily, preferably in solid or liquid unit dosages of about 0.01 mg–1 g of virucide together with about 0.1–10 g of a pharmaceutically acceptable carrier. The precise dosages and frequencies of administration will vary in relation to the severity of the clinical symptoms and the nature of the virucide and of the virus species being treated, as well as the nature and size of the subject, in a manner well known to veterinary and clinical practitioners.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

Preparation of cod Liver Oil Hydrolysate

A 100 ml quantity of medicinal grade cod liver oil (CLO), obtained from Humco Laboratories, was combined with 100 ml of 10% aqueous sodium hydroxide and refluxed for two hours. After cooling, the mixture was acidified with 50% sulfuric acid. The acidified reaction mixture was extracted with ether and the ether layer was washed with water until the wash water was neutral. The ether extract was dried over anhydrous sodium sulfate, filtered, and the ether removed on a rotatory evaporator, to yield 87 ml of a yellow oil. The oil was then combined with an equal volume of 50% potassium hydroxide and heated at reflux for two hours. The resultant reaction mixture was acidified with 50% sulfuric acid and extracted three times with 250 ml portions of ether. The combined ether extracts were washed with water until the wash water was neutral. After drying over anhydrous sodium sulfate, filtering and removing the ether, 56.3 g of CLO hydrolysate (CLOH) was obtained.

An ultraviolet spectrum of the product showed long wavelength absorption, indicating that at least partial conjugation of the double bonds had occurred. The yellow oil obtained prior to the 50% KOH treatment, consisting mainly of unconjugated fatty acids, can also be used as a source of virucide according to the invention, either as such or after further purification, e.g., as shown in Example 2.

It is also possible to obtain a virucidally active concentrate by extracting a fish liver oil, e.g., cod liver oil, with an alcohol, e.g., methanol, and evaporating the alcohol, and optionally saponifying as above and recovering the resultant hydrolysate, which can be further purified, e.g., as in Example 2.

EXAMPLE 2

Fractionation of Cod Liver Oil Hydrolysate

A 1 g sample of the CLOH prepared in Example 1, dissolved in 1 ml of acetonitrile, was chromatographed using reverse phase high performance liquid chromatography (RP-HPLC), using a Chrompack Lichrosorb 10 RP 18 column, 25 cm in length, with 100% acetonitrile mobile phase. The collected fractions were stripped of acetonitrile and weighed. A fraction having a retention time of 2.3 min. and weighing 78.7 mg was produced, and labelled CLOH-2.3.

A portion of the CLOH-2.3 material weighing 63.0 mg was dissolved in 400 μl of mobile phase and rechromatographed using 90% acetonitrile/10% water. Three major peaks resulted, which were separately collected and the solvent stripped. The amounts obtained after vacuum stripping were: Peak 1, 7.9 mg; Peak 2, 6.2 mg; and Peak 3, 16.0 mg. The peaks were labelled CLOH-2.3-1, CLOH-2.3-2 and CLOH-2.3-3, respectively.

In a separate experiment, it was found that extraction of CLO with methanol, followed by evaporation of the methanol and further extraction of the residual extract with acetonitrile produced a solution which, upon RP-HPLC chromatography, was shown to contain major quantities of materials having the same retention times as the major components in the CLOH-2.3 material. By judicious isolation of RP-HPLC fractions, it was possible to produce a concentrate having very similar chromatographic behavior on RP-HPLC to the CLOH-2.3 material, although the yield of such fractions was substantially lower than the yield of concentrate from fractionation of CLOH.

In a further experiment, enrichment of the CLOH material in the CLOH-2.3 fraction components was effected by extracting a 37.4 g sample of CLOH with three equal volumes of about 15 ml each of acetonitrile. The combined extracts were stripped and weighed, producing 15.1 g of residue, which was redissolved in acetonitrile to a concentration of 1 g/3 ml. RP-HPLC of this material using 100% acetonitrile as the mobile phase showed that the major peak had a retention time of 2.3 minutes, and represented a sustantially greater percentage of the total material in the sample than was the case in the CLOH itself. Accordingly, repetitive injections of this material were made and an additional stock of the CLOH-2.3 fraction was prepared. Further fractionation of the CLOH-2.3 material using 90/10 acetonitrile/water was effected as described above, and material corresponding to CLOH-2.3-3 was collected and vacuum stripped.

EXAMPLE 3

In Vitro Bioassays

Assays were performed using herpes simplex virus type 2 (HSV-2).

Production of Virus Test Materials

Cell Culture. Cell cultures used for the propagation and titration of HSV-2 were the human diploid lung embryonic line MRC-5 and the human malignant epitheloid cell line HEP-2 respectively. Stock monolayer cultures of both cell lines were propagated in Dulbecco's Modified Eagle's medium (DME) supplemented with 10% (V/V) calf serum. Spinner cultures for mass production of HEP-2 cells were grown in Joklik's medium supplemented with 10% (V/V) calf serum and 1% (W/V) pluronic acid. Monolayer cultures of HEP-2 cells for plaque or virucidal assay were seeded into 60 mm dishes in DME supplemented with 10% calf serum and antibiotics. Stock cultures were maintained in antibiotic free medium.

Preparation of HSV-2 Stock and Titration

Herpes simplex virus, type 2 (HSV-2) strain 333 was obtained from Dr. John Hughes of the Dept. of Medical Microbiology, College of Medicine, The Ohio State University. Stocks of HSV-2 were prepared in the human diploid embryonic lung cell line, MRC-5. Confluent MRC-5 monolayer cultures in T-75 plastic flasks were washed one time with Hank's and Balanced Salt solution (HBSS) and infected with 0.5 ml of HSV-2, strain 333 stock. Virus was adsorbed for 1 hour at 37° C. Then the culture was refed with 15 ml of DME supplemented with 1% (V/V) calf serum. Virus was harvested 48 hours later when cytopathology was complete. Cultures were frozen and thawed rapidly three times to release cell associated virus, clarified by centrifugation at 10,000×g for 15 minutes at 4° C., aliquoted into 5 ml lots and frozen at −70° C. One lot was taken for virus titration.

HSV-2 was titrated by plaque assay in HEP-2 cells under a semi-solid methyl cellulose overlay. Tenfold serial dilutions of virus were prepared in HBSS and 0.3 ml aliquots of each dilution inoculated onto triplicate HEP-2 cell monolayers in 60 mm plastic petri dishes. Adsorption of virus was for 1 hour at 37° C. Plates were then overlayed with 5 ml of a 1:1 mixture of 2×DME supplemented with 2% (V/V) calf serum and 3% (W/V) methyl cellulose to give a final 1×DME supplemented with 1% calf serum and 1.5% methylcellulose. Infected plates were incubated at 37° C. in a humidified 10% $CO_2$ atmosphere for 48 hours. Virus plaques were visualized by staining with crystal violet and counted under a dissecting microscope. Virus titers were calculated from the plaque numbers by averaging the plaque count and multiplying by 3.3 (0.3 ml plates).

Technique for Virus Assays

The following procedure was employed to assay virucidal activity in various test samples. Compounds were received as a solution in DMSO and were serially diluted in HBSS as described for each experiment. For the test, 1 ml of each dilution was mixed with 1 ml of a stock virus suspension diluted to approximately $9 \times 10^3$ plaque forming units (P.F.U.)/ml. This test mixture was incubated at 25° C. for 30 minutes, then inoculated onto a cell culture (HEP-2) for plaque assay as described previously. Mock treated (virus plus HBSS) controls were included with each test. Any reduction of plaque titer by test compounds as compared to the mock treated control was indicative of virucidal activity. Minimal inhibitory concentrations (MIC) of test compounds were defined as the lowest concentration of a compound capable of producing a 3-log (1000-fold) reduction in virus titer.

Bioassay of CLOH and Fractionation Products

Samples from RP-HPLC fractionation of the CLOH, produced according to Example 2, as well as purified samples of palmitic, myristic and oleic acids and Vitamin $D_2$, were tested for HSV-2 bioactivity. The results of this bioassay are listed in Table 1. The CLOH-2.3 sample was shown to have an MIC value at least as low as 2.45 μg/ml; the breakpoint was not reached at dilutions of 1:6400. MIC values are shown in Table 2. The CLOH-2.3-3 sample had an MIC of 2.5 μg/ml. Pure oleic acid was not active in this assay, nor were palmitic and myristic acids and Vitamin $D_2$.

Spectral data indicated that the CLOH-2.3-3 material was likely to be a mixture of EPA and DHA. Accordingly, authentic samples of EPA and DHA were obtained from Sigma Chemical Company and their presence was confirmed as major components, together with impurities in the CLOH-2.3-3 fraction. Authentic EPA and DHA and their methyl esters were submitted for bioassay. The samples were prepared with DMSO/HBSS (50:50) to a concentration of 8 mg/ml and assayed at several dilutions. Results of the bioassay are shown in Table 3 and the MIC values for the samples are shown in Table 4.

TABLE 1

RESULTS OF HSV-2 BIOASSAY OF SELECTED PURIFIED ACIDS, VITAMIN $D_2$ AND RP-HPLC FRACTIONS OF CLO-HYDROLYSATE

| Dilutions | Palmitic acid[a] plaque count | titer | Vitamin D[a] plaque count | titer | Oleic acid[a] plaque count | titer | Myristic[a] plaque count | titer |
|---|---|---|---|---|---|---|---|---|
| 1:10 | TNTC[c] | — | TNTC | — | 36 | $1.2 \times 10^2$ | TNTC | — |
| 1:100 | " | | " | | TNTC | | " | |
| 1:200 | " | | " | | " | | " | |
| 1:400 | " | | " | | " | | " | |
| 1:800 | " | | " | | " | | " | |
| 1:1600 | " | | " | | " | | " | |
| 1:3200 | " | | " | | " | | " | |
| 1:6400 | " | | " | | " | | " | |

| Dilutions | CLOH-2.3 plaque count | titer | CLOH-2.3-1 plaque count | titer | CLOH-2.3-2 plaque count | titer | CLOH-2.3-3 plaque count | titer |
|---|---|---|---|---|---|---|---|---|
| 1:10 | 0 | 0 | 0 | 0 | 0 | 0 | 0 | 0 |
| 1:100 | 1 | $3.3 \times 10^0$ | 0 | 0 | 0 | 0 | 0 | 0 |
| 1:200 | 1 | $3.3 \times 10^0$ | 2 | $6.6 \times 10^0$ | 0 | 0 | 0 | 0 |
| 1:400 | 0 | 0 | 14 | $4.6 \times 10^1$ | 1 | $3.3 \times 10^0$ | 1 | $3.3 \times 10^0$ |
| 1:800 | 1 | $3.3 \times 10^0$ | 30 | $9.9 \times 10^1$ | 1 | $3.3 \times 10^0$ | 0 | 0 |
| 1:1600 | 0 | 0 | 116 | $3.8 \times 10^2$ | 1 | $3.3 \times 10^0$ | 2 | $6.6 \times 10^0$ |
| 1:3200 | 0 | 0 | TNTC | — | 2 | $6.6 \times 10^0$ | 10 | $3.3 \times 10^1$ |
| 1:6400 | 0 | 0 | " | — | 4 | $1.3 \times 10^1$ | 27 | $8.9 \times 10^1$ |

[a] Control $2.6 \times 10^4$
[b] Control $1.3 \times 10^4$
[c] Too numerous to count

TABLE 2

MIC RESULTS FOR HSV-2 BIOASSAY OF SELECTED PURIFIED ACIDS, VITAMIN $D_2$ AND RP-HPLC FRACTIONS OF CLO HYDROLYSATE

| Sample | Wt. of sample in mg | Dilution showing 3 log reduction | MIC value μg/ml |
|---|---|---|---|
| Palmitic acid | 5.9 | — | — |
| Vitamin $D_2$ | 5.0 | — | — |
| Oleic acid | 5.0 | — | — |
| Myristic acid | 5.9 | — | — |
| CLOH-2.3 | 15.7 | 1:6400 | 2.45 |
| CLOH-2.3-1 | 7.9 | 1:200 | 39.5 |
| CLOH-2.3-2 | 6.2 | 1:1600 | 3.9 |
| CLOH-2.3-3 | 16.0 | 1:6400 | 2.5 |

TABLE 3

HSV-2 ASSAY RESULTS FOR AUTHENTIC STANDARDS AND RP-HPLC ISOLATED FRACTIONS

| | (EPA) | | (DHA) | | CLOH-2.3-3 | | DHA—ME | | EPA—ME | | CLOH-2.3 | |
|---|---|---|---|---|---|---|---|---|---|---|---|---|
| Dilution | plaque count | titer | plaque count | titer | plaque count | titer | plaque count | titer | plaque count | titer | plaque count | titer |
| 1:10 | 0 | 0 | 0 | 0 | 0 | 0 | 95 | $3.1 \times 10^2$ | 0 | 0 | 0 | 0 |
| 1:100 | 0.5 | $1.7 \times 10^0$ | 0 | 0 | 0 | 0 | 293 | $9.7 \times 10^2$ | 2.5 | $8.3 \times 10^0$ | 0 | 0 |
| 1:400 | 0.5 | $1.7 \times 10^0$ | 0 | 0 | 0 | 0 | TNTC | TNTC | 7.5 | $2.5 \times 10^1$ | 0 | 0 |
| 1:800 | 0.5 | $1.7 \times 10^0$ | 0 | 0 | 0 | 0 | TNTC | TNTC | 13.5 | $4.5 \times 10^1$ | 0 | 0 |
| 1:1600 | 0.5 | $1.7 \times 10^0$ | 0 | 0 | 0 | 0 | " | " | 19.5 | $6.4 \times 10^1$ | 0 | 0 |
| 1:3200 | 0.5 | $1.7 \times 10^0$ | 0 | 0 | 0 | 0 | " | " | 42.5 | $1.4 \times 10^2$ | 0 | 0 |
| 1:6400 | 0.5 | $1.7 \times 10^0$ | 0 | 0 | 0.5 | $1.7 \times 10$ | " | " | 36.5 | $1.2 \times 10^2$ | 1 | $3.3 \times 10^0$ |
| 1:12800 | 0.5 | $1.7 \times 10^0$ | 0 | 0 | 0 | 0 | " | " | 66 | $2.2 \times 10^2$ | 2.5 | $8.3 \times 10^0$ | control: dilution, 1:100; plaque count, 13.5; titer, $4.5 \times 10^3$

EPA = eicosapentaenoic acid
EPA—ME = eicosapentaenoic acid, methyl ester
DHA = docosahexaenoic acid
DHA—ME = docasahexaenoic acid, methyl ester

TABLE 4

MIC VALUES FOR AUTHENTIC STANDARDS AND RP-HPLC ISOLATED FRACTIONS

| Sample | Wt. of Sample in mg. | Dilution Showing 3 log reduction | MIC µg/ml |
|---|---|---|---|
| EPA | 4.7 | 1:12800 | 0.37 |
| DHA | 6.0 | 1:12800 | 0.47 |
| CLOH-2.3-3 | 5.4 | 1:12800 | 0.42 |
| DHA—ME | 5.9 | — | — |
| EPA—ME | 5.4 | 1:10 | 540 |
| CLOH-2.3 | 6.4 | 1:6400 | 1.00 |

The in vitro bioassays demonstrated that the polyunsaturated acids, exemplified by EPA and DHA, both in their unconjugated and at least partially conjugated forms, are potent and fast-acting virucides. Separate experiments showed that DHA inhibits more than 98% of the virus within 30 seconds of contact, and better than 99.99% of the virus within 30 minutes of contact.

Comparable results are expected for in vitro activity of the polyunsaturated alcohols, aldehydes and acid salts of the invention.

EXAMPLE 4

In Vivo Bioassays

Using substantially the procedures of Pancic et al., loc. cit., the topical activity of DHA, a representative and preferred virucide for use in the present method, was evaluated in mice and in guinea pigs. Both evaluations included comparative testing against ACV and the mouse tests included a comparison of two different vehicles.

Mouse Bioassay

The antiherpetic activity of DHA and ACV was compared using two evaluation criteria; (1) duration and severity of genital lesions, and (2) increased or decreased survival time.

The experimental groups were:
A. HSV-2 infected DHA treated
   (1) Two doses: 1 mg/ml Low and 10 mg/ml High
   (2) Two vehicles per dose: ointment and soluble form of the drug
B. HSV-2 infected, Acyclovir treated
   (1) One dose of the drug
   (2) Two vehicles (as above)
C. HSV-2 infected (infected controls)
   (1) Vehicle control (two vehicles)
   (2) No treatment
D. Uninfected mice
   (1) Vehicle alone
   (2) Vehicles and drug (high dose only)
   (3) Untreated This experimental approach provided an indication of whether or not DHA exhibited antiherpetic activity in vivo, as compared to a known active drug Acyclovir. Protocols and treatment regimens are shown below.

Animals

Female Swiss Webster mice were received from Charles River Breeding Laboratories, Inc. at 5 weeks of age and were held in quarantine for two weeks. Pooled sera from selected mice was tested for Pneumonia Virus of Mice, Mouse Hepatitis Virus, Sendai Virus, and Lymphocytic Choriomeningitis Virus. No significant titers were found.

Mice were 7 weeks of age at the beginning of the experiment, were housed 5 per cage, and allowed food and water ad libitum.

HSV-2 Stock Virus Preparation and Titration

HSV-2 strain 333 passaged in MRC-5 cells was inoculated onto confluent HEP-2 monolayers and harvested 48 hours later when 100% of the cells exhibited cytopathology. The cells were disrupted by freezing and thawing three times and the supernatant clarified by centrifuging at $1000 \times g$ for 10 minutes and by centrifuging again at $8,000 \times g$ rpm for 10 minutes at 40° C. Virus containing supernatant was aliquoted and frozen at −70° C.

The virus was titrated on confluent HEP-2 monolayers seeded from Spinner culture 24 hours earlier at $2 \times 10^6$ cells per 60 mm tissue culture dish. Serial tenfold dilutions of the virus stock were prepared in HBSS and each dilution was inoculated in triplicate onto HEP2 cell monolayers and allowed to adsorb for 60 minutes at 37° C., 10% $CO_2$. Following adsorption the plates were overlayed with a 3% methylcellulose overlay in Dulbecco's Modified Eagle's Medium +20% calf serum and incubated at 37° C., 10% $CO_2$ for 48 hours and subsequently stained with crystal violet. Plaques were counted with the aid of a microscope, and the titer of the stock virus preparation was $4.4 \times 10^8$ p.f.u./ml.

Virus Infection of Mice

Pre-Treatment with 0.1N NaOH. 24 hours before inoculation with HSV-2 virus, mice were washed intravaginally with sterile 0.1N NaOH to irritate the vaginal tissue. 0.15 ml 0.1N NaOH was introduced intravaginally with a sterile eye dropper and the area flushed three times. Two hours prior to virus inoculation mice were swabbed intravaginally with 0.1N NaOH, using a sterile cotton swab.

Virus Inoculation. An aliquot of HSV-2 suspension in HBSS was thawed quickly and diluted 1:10 in HBSS. 0.020 ml of the diluted virus suspension was introduced intravaginally using an Eppendorf pipet with separate, sterile Eppendorf pipet tips for each mouse. The inoculation was done in a biohazard hood. Each infected mouse received $1 \times 10^7$ p.f.u. of HSV-2.

Drug Preparation

Vehicles. A 70% dimethyl sulfoxide (DMSO)—30% HBSS solution or polyethylene glycol 1000 (PEG) served as carriers for the Acyclovir or DHA and were also administered alone, as controls. The DMSO-HBSS vehicle was selected based on the observed (visually) solubility of DHA in various DMSO-HBSS solutions. 1 mg DHA was soluble in 1 ml of 70% DMSO-30% HBSS.

Acyclovir. A 5% weight/volume mixture of unionized Acyclovir or the sodium salt of Acyclovir was prepared in 70% DMSO-30% HBSS and in PEG 1000. The PEG 1000 was warmed to facilitate uniform suspension of the drugs. The use of the sodium salt of Acyclovir in either carrier required the addition of 1N HCL to neutralize the mixtures.

4,7,10,13,16,19 Docosahexaenoic Acid (DHA). A weight/volume mixture of 1 mg DHA per ml carrier or 10 mg per ml carrier constitute the low and high doses of test drug prepared. The PEG 1000 was warmed to facilitate mixing.

Drug Administration and Animal Observations

Control and infected mice were treated in a biohazard hood with carrier plus drug or carrier alone twice daily Monday through Friday and once daily Saturdays and Sundays. The treatment regimen was initiated three hours post HSV-2 intravaginal inoculation and was continued for 14 days thereafter. DMSO-HBSS alone or DMSO-HBSS plus drug was delivered at 0.15 to 0.2 ml per mouse, using separate, sterile eye droppers. PEG 1000 alone or PEG 1000 plus drug was warmed and delivered at approximately 0.15 ml per mouse, using separate, sterile swabs.

Infected and control mice were allowed food and water ad libitum and were observed once daily for clinical signs of virus infection for 14–21 days following HSV-2 innoculation. Vaginal HSV-2 infection was scored according to the following description. A score of 0 indicated no clinical signs of vaginal infection. A score of ± indicated slight perivaginal redness. A score of 1 indicated perivaginal redness and swelling of 1–2 mm. A score of 2 indicated perivaginal redness and swelling of 2–3 mm. A score of 3 indicated perivaginal and perianal redness and swelling of 3–4 mm. A score of 4 indicated perivaginal and perianal redness and swelling of 4 mm or more, with exudate.

The results are summarized in Tables 5 and 6. It is seen that DHA showed effective virucidal activity against HSV-2, especially the low dose ointment preparation. The validity of this test procedure is shown by the fact that ACV was effective in minimizing the clinical signs of infection in either carrier vehicle and in achieving a survival rate of 100% in both groups within the observed 14 day period. It should also be noted that neither carrier or any of the preparations showed signs of toxicity in the tested animals.

Guinea Pig Bioassay

A blind comparative test was carried out on guinea pigs using coded substances labeled A through D. The testers were told only that one of the four substances was ACV, that the other three coded samples were the same material, in concentrations of 0.1, 1.0 and 10 mg/ml, and that all four samples were formulated in a polyethylene glycol 1000 (PEG-1000) vehicle. A separate sample of the PEG-1000 was also submitted to serve as a placebo for treating virus control animals. The materials and experimental protocol is shown below.

Animals. Female Hartley strain albino guinea pigs weighing about 450–500 g were used. The animals were quarantined 24 hr prior to use in this study, and maintained 5 to a 32"×32"×9" stainless steel cage on Wayne guinea pig diet and water ad libitum.

Virus. Strain E194 of herpes virus type 2 was used. The virus was initially obtained from Dr. M. Fiala, Harbor General Hospital, (Torrance, CA), and an MA-104 culture pool was prepared and pretitered in guinea pigs. The virus was held at −90° C. until used.

TABLE 5

| | | | | | | | | | |
|---|---|---|---|---|---|---|---|---|---|
| | IN VIVO MOUSE BIOASSAY | | | | | | | | |
| | | | | TREATMENT | | | | | |
| | NO TREATMENT | VEHICLE* | | ACYCLOVIR (5% wt/vol) | | High DHA (10 mg/ml) | | Low DHA (1 mg/ml) | |
| RESULTS | (control) | PEG | DMSO | PEG | DMSO | PEG | DMSO | PEG | DMSO |
| # Animals/Group | 10 | 10 | 10 | 10 | 10 | 10 | 10 | 10 | 10 |
| # Infected, Day 14 | 6 | 5 | 8 | 4 | 3 | 5 | 4 | 1 | 4 |
| # of Deaths, Day 14 | 4 | 3 | 5 | 0 | 0 | 3 | 2 | 0 | 2 |
| Max. Lesion Score** | +4 | +4 | +4 | ± | ± | ± to +3 | ± to +3 | ± | ± to +1 |

*PEG = Polyethylene Glycol
DMSO = Dimethylsulfoxide
**Lesion Scoring System

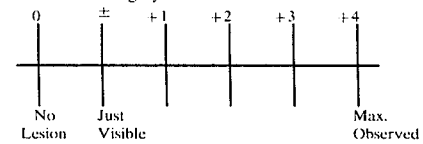

TABLE 6
IN VIVO MOUSE BIOASSAY

| Group | Mean Day of Death | % Mortality | Maximum % Morbidity (Day) |
| --- | --- | --- | --- |
| DMSO, Control | 9.8 | 40 | 80 (8) |
| DMSO & High DHA | 8.5 | 20 | 40 (7) |
| DMSO & Low DHA | 11.7 | 30 | 40 (7) |
| Ointment, Control | 10.3 | 30 | 50 (7) |
| Ointment & High DHA | 11.7 | 30 | 50 (7) |
| Ointment & Low DHA | >14 | 0 | 10 (6) |
| DMSO & Acyclovir | >14 | 0 | 30 (7) |
| Ointment & Acyclovir | >14 | 0 | 40 (7) |
| HSV-2 Control | 9.5 | 40 | 60 (8) |

Drugs. The substances tested consisted of four bottles labelled "A", "B", "C", and "D" with no identifying key. The samples were: A, 0.1 mg/ml DHA (0.003 mmol/ml); B, 5% w/w ACV (0.22 mmol/ml); C, 1 mg/ml DHA (0.03 mmol/ml); and D, 10 mg/ml DHA (0.3 mmol/mg). Each substance, at room temperature, had a hard wax consistency, so was warmed to 45° C. in a water bath and gently mixed immediately prior to use in treatment. All were treated as light-sensitive compounds.

Experimental Protocol. The guinea pigs were infected by applying a virus-soaked swab intravaginally, with agitation, for 20 seconds. Toxicity control animals were similar pretreated using swabs soaked in sterile Puck's balanced salt solution. Treatment began 20 hr later, with the compound or placebo applied topically intravaginally, perivaginally, and perianally using cotton swabs soaked in the respective substance. Treatment continued three times daily (8 a.m., noon, 4 p.m.) for 7 days. Ten infected animals were used for each coded substance, with twenty used for virus controls. Five sham-infected animals were concomitantly treated with each coded substance to serve as toxicity controls. Two guinea pigs were held separately to serve as normal untreated controls.

Each animal was observed daily for survival for a total of 28 days. On days 5 through 8 post-virus inoculation, the genital area was carefully examined and signs of irritation in the toxicity controls and lesion severity in injected animals was scored on a 0 to 4 scale using the same scale as in the mouse bioassay. The results were scored as average daily lesion (ADL) scores for each group, and as mean vaginal lesion (MVL) scores, calculated as the mean of the ADL scores for days 5–8. The maximum mean score for the toxicity control animals was also determined.

On day 6 prior to the 8 a.m. treatment, intravaginal and perivaginal areas of each infected guinea pig were uniformly swabbed with sterile cotton swabs. The swab for each animal was placed in 1.0 ml of sterile Eagles minimum essential medium and immediately frozen at −90° C.; several days later all were thawed and each swab-containing sample vortexed for 15 seconds and then the sample was diluted through a series of 10-fold dilutions in sterile medium. Each dilution was assayed for virus in triplicate by adding 0.1 ml to an established monolayer of MA-104 cells in 96-well disposable plastic microplates. The plates were sealed, incubated at 72 hr at 37° C., and virus-induced cytopathic effect noted microscopically.

Data Analysis. Increases in survivors were analyzed using chi square analysis with Yate's correction. Mean survival times (MST) of animals dying on or before day 29 were determined for each group, and evaluated using the t test. Titers of virus recovered from vaginal areas were expressed as 50% cell culture infectious dosages calculated using the Reed-Muench procedure, and titer decreases evaluated by t test.

The results are summarized in Table 7. This experiment used a high level of virus to infect the animals, which was selected to induce eventual deaths in all of the infected animals. As a consequence, the total survival and mean survival time data were of considerably less significance than the effect on the severity of lesions and on the vaginal virus titer. In this experiment, neither ACV nor the lowest dosage of DHA were able to achieve a statistically significant reduction in lesion scores. Animals receiving the higher dosages of DHA of samples "C" and "D" had statistically significant reductions in lesion scores. Significant decreases in vaginal virus titer were seen in all the treated groups compared to the placebo treated group.

TABLE 7
COMPARATIVE BIOASSAY WITH TOPICAL ADMINISTRATION

| | Toxicity Controls | | Infected, Treated | | | | | | | |
| --- | --- | --- | --- | --- | --- | --- | --- | --- | --- | --- |
| Treatment Group | Surv/Total | Max. Irrit. Score | Surv/Total | MST (days) | MVL Scores Days 5–8 | MVL Score Day 5 | MVL Score Day 6 | MVL Score Day 7 | MVL Score Day 8 | Vag. Virus Titer |
| "A" | 5/5 | 0.0 | 6/10 | 12.3 | 3.2 | 2.4 | 3.0 | 3.5 | 3.8 | $10^{2.3}$** |
| "B" | 5/5 | 0.0 | 5/10 | 11.6 | 2.8 | 1.8 | 2.3* | 3.4 | 3.3 | $10^{2.3}$** |
| "C" | 5/5 | 0.0 | 4/10 | 13.3 | 2.4* | 1.7 | 2.3* | 2.8 | 3.1 | $10^{2.4}$** |
| "D" | 5/5 | 0.0 | 8/10 | 16.5 | 2.4* | 1.5* | 2.1* | 3.0 | 3.1 | $10^{3.1}$* |
| Placebo | | | 13/20 | 14.3 | 2.8 | 2.1 | 2.7 | 3.0 | 3.2 | $10^{3.7}$ |
| Normals | | 0.0 | 2/2 | >21.0 | 0.0 | 0.0 | 0.0 | 0.0 | 0.0 | |

*P < 0.05
**P < 0.001

No topical irritation was observed in any drug-treated group.

EXAMPLE 5

Ointment Formulation

An ointment suitable for administration according to the method of the invention is prepared as follows. The ointment is designed for topical administration to skin and mucus membrane surfaces which are infected with enveloped virus. The ointment should be gently rubbed on the affected area until it disappears. The frequency of administration and variations in dosage will depend on the clinical indications.

| DHA | 1 g |
| --- | --- |
| PEG-1000 | 1,000 ml |

The PEG-1000 is warmed to about 45° C. in a water bath until it melts and liquifies. The DHA is then added and blended to achieve homogeniety. Optionally, other ingredients may be added to modify the composition, e.g., stabilizers, emollients and the like.

EXAMPLE 6

IM Injectable Formulation

A preparation suitable for intramuscular injection according to the method of the invention as prepared as follows.

| DHA | 10 mg |
|---|---|
| Butylated hydroxyanisole | 0.01% w/v |
| Butylated hydroxytoluene | 0.01% w/v |
| Peanut Oil or Sesame Oil sufficient to make | 1.0 ml |

The ingredients are blended, the blended ingredients are placed in an ampoule, which is sterilized and sealed.

EXAMPLE 7

Powder Formulation

A powder for use on areas affected by virus infections and suitable for administration according to the method of the invention is prepared as follows:

| DHA | 5% w/w |
|---|---|
| Silicon dioxide, anhydrous | 0.5% w/w |
| Corn starch, lactose, fine powder- each, with the total sufficient to make | 1 kg |

The ingredients are mixed and blended to form a powder composition suitable for topical application according to the invention. It will be understood that other ingredients, e.g., perfumes and/or preservatives, may be incorporated in the composition.

EXAMPLE 8

Disinfectant Spray Formulation

A spray which may be applied to the hands, the skin and/or mucus membranes, and which is also suitable for disinfectant use on instruments, examining tables, toilet seats and other surfaces upon which virus may be deposited, is prepared as follows:

| DHA | 25 g |
|---|---|
| Butylated hydroxyanisole | 4.0 mg |
| Poloxamer 235 (poly(oxypropylene)-poly(oxyethylene) copolymer surfactant, Av. M.W. 46,000) | 25.0 g |
| Benzyl alcohol | 4.7 ml |
| Isotonic saline | 500.0 ml |

300 ml of isotonic saline are combined with the poloxamer 235 and thoroughly mixed, after which the DHA, the butylated hydroxyanisole and the benzyl alcohol are added and thoroughly mixed. Additional isotonic saline is added to make up the volume to 500 ml. It will be understood that other ingredients may be added to this formulation and the amount of virucide may be varied as a function of the intended use to which the spray is put. The spray may be packaged in pump dispenser bottles or in a spray can together with an environmentally acceptable propellant, under pressure.

EXAMPLE 9

Tablet Formulation

A tablet suitable for administration according to the method of the invention is prepared as follows. Each dosage unit is designed for administration to a patient weighting about 80 kg. The frequency of administration of the illustrated tablets will depend upon the type of virus infection being treated, the severity of the symptoms and the nature of the subject being treated.

| EPA | 200 g |
|---|---|
| Wheat starch | 26 g |
| Lactose | 76 g |
| Magnesium stearate | 6 g |

A granulation obtained upon mixing lactose with a portion of the starch and granulated starch paste made from the remainder of the starch is dried, screened and mixed with the EPA and the magnesium stearate. The mixture is compressed into 1000 tablets weighing about 308 mg each. It will be understood that a dragee or a capsule may be used in place of a tablet, and it may be prepared by conventional techniques.

The preceding examples can be repeated with similar success by substituting the generically or specifically described reactants and/or operating conditions o of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of inactivating enveloped virus, which comprises contacting said virus with a virucidally effective amount of a $C_{20-24}$ linear polyunsaturated acid, aldehyde or primary alcohol having 5-7 double bonds, a pharmaceutically acceptable salt of said acid, or a mixture thereof.

2. The method of claim 1, wherein the virucidal agent is a $C_{20-24}$ linear polyunsaturated acid having 5-7 double bonds or a mixture of said acids.

3. The method of claim 2, wherein said acid is eicosapentaenoic acid (EPA), docosahexaenoic acid (DHA) or a mixture thereof.

4. The method of claim 2, wherein the acids are 5,8,11,14,17-EPA and 4,7,10,13,16,19-DHA.

5. The method of any of claims 1-4, wherein the virus is herpes simplex.

6. The method of any of claims 1-4, wherein the virus is herpes simplex type 2.

7. The method of claim 5, wherein the virucidal agent is applied topically to reduce or inhibit lesions in an animal or human suffering from a herpes simplex virus infection.

8. The method of claim 1, wherein said effective amount is about 0.001 mg-1 g per administration.

9. The method of claim 7, wherein said effective amount is about 0.1-100 mg per application.

10. The method of claim 2, wherein said acid is applied as a topical preparation having a triglycerides content of less than 50% by weight relative to said acids.

11. The method of claim 10, wherein said triglycerides content is less than 30%.

12. The method of claim 10, wherein said topical preparation is substantially free of triglycerides of said acids.

13. The method of any of claims 10-12, wherein said topical preparation is an ointment, cream, salve, gel or lotion.

14. The method of claim 13, wherein said topical preparation is an ointment.

15. The method of claim 14, wherein said effective amount is about 0.01-50 mg of virucide per cc of ointment base, and about 0.01-100 mg of virucide per dose.

16. The method of claim 15, wherein about 0.1-10 mg of EPA, DHA or a mixture thereof per cc of ointment base is present in said preparation.

* * * * *